United States Patent [19]
Das et al.

[11] Patent Number: 5,900,376
[45] Date of Patent: May 4, 1999

[54] AGENT FOR PROTEIN PRECIPITATION, A METHOD OF PROTEIN PRECIPITATION, A METHOD OF PROTEIN ASSAY USING PROTEIN PRECIPITATION AGENT, AND A KIT FOR PROTEIN ASSAY

[75] Inventors: Manik Lal Das; Aftab Alam, both of St. Louis, Mo.

[73] Assignee: Geno Technology, Inc., St. Louis, Mo.

[21] Appl. No.: 08/965,873

[22] Filed: Nov. 7, 1997

[51] Int. Cl.$^6$ ...................................... G01N 33/00
[52] U.S. Cl. ............................ 436/86; 436/166; 436/177; 436/808; 530/418; 530/419; 530/420; 530/427
[58] Field of Search ............................ 436/86, 166, 177, 436/808; 422/61, 68.1, 72; 530/418, 419, 420, 427

[56] References Cited

U.S. PATENT DOCUMENTS

| | | | |
|---|---|---|---|
| 5,089,602 | 2/1992 | Isleker et al. | 530/359 |
| 5,231,034 | 7/1993 | Fleming | 436/169 |
| 5,300,440 | 4/1994 | Alam | 436/86 |

OTHER PUBLICATIONS

Bensadoun et al., *Analytical Biochemistry*, vol. 70, pp. 241–250, 1976.

Brown et al., *Analytical Biochemistry*, vol. 180, pp. 136–139, 1989.

Peterson, *Analytical Biochemistry*, vol. 83, pp. 346–356, 1977.

*Primary Examiner*—Cecilia J. Tsang
*Assistant Examiner*—Abdel A. Mohamed
*Attorney, Agent, or Firm*—Nikaido, Marmelstein, Murray & Oram, LLP

[57] ABSTRACT

A method of a protein assay wherein a protein solution is treated with an acidic component followed by the addition of a precipitate-forming component, which results in precipitation of protein. The protein precipitate is collected and treated with one or more reagents of a protein assay to produce a characteristic protein color reaction. The concentration of protein is determined by measuring the optical density of protein color reaction and comparing the color reaction with a known standard.

15 Claims, 3 Drawing Sheets

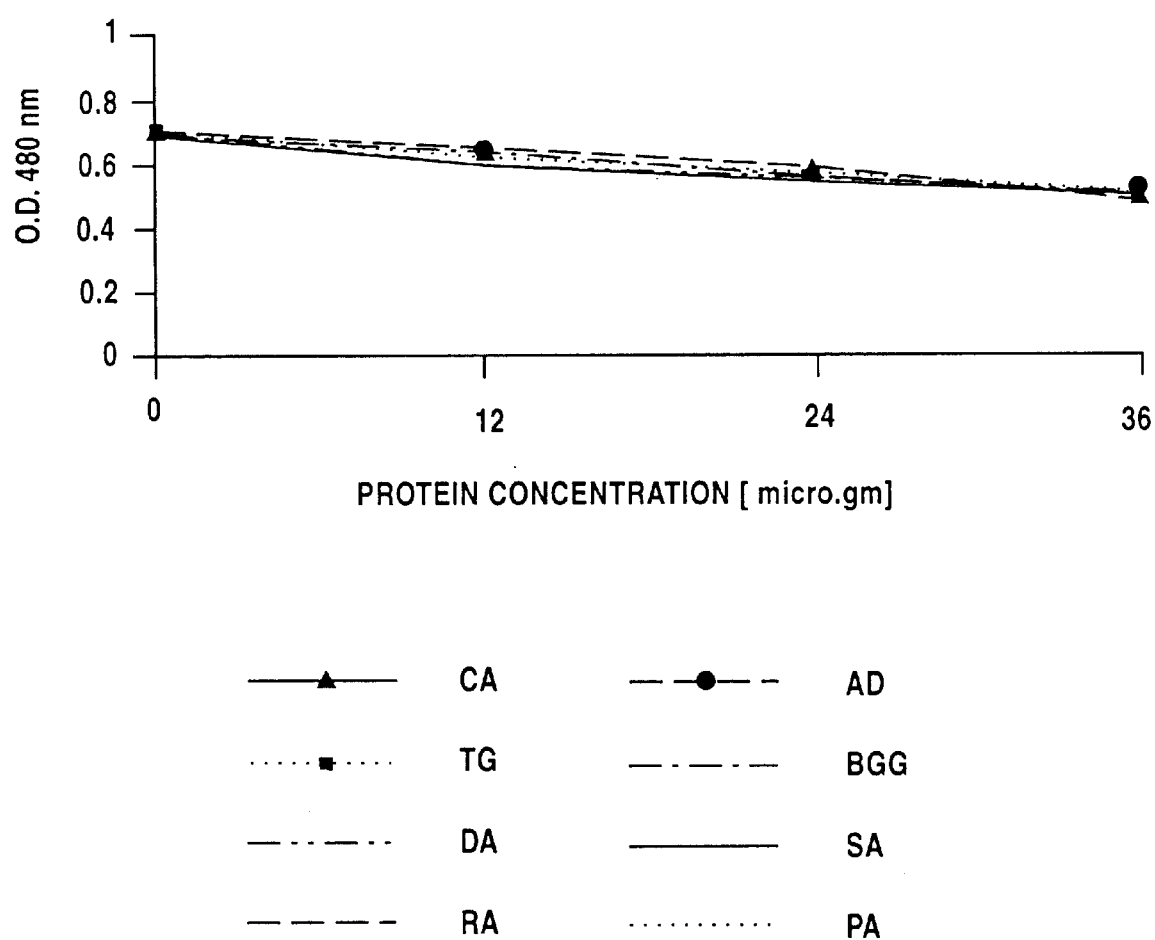

5,900,376

AGENT FOR PROTEIN PRECIPITATION, A METHOD OF PROTEIN PRECIPITATION, A METHOD OF PROTEIN ASSAY USING PROTEIN PRECIPITATION AGENT, AND A KIT FOR PROTEIN ASSAY

HISTORY OF THE INVENTION

Precipitation of protein is a useful method in study and use of protein. There are several protein precipitation methods currently in use, unfortunately, they all suffer from serious limitations. One of the most widely used methods of protein precipitation uses trichloroacetic acid (TCA). When a protein solution is mixed with a solution of TCA, protein precipitates. Unfortunately, TCA induced precipitation of protein is not always quantitative. When TCA is added to a protein solution containing protein whose concentration could be measured in several milligrams per milliliter, most of the protein in solution is indeed precipitated. However, precipitation is not complete and a small amount of protein is left behind in solution that fails to precipitate in response to TCA or other acids. If on the other hand, a protein solution contains only microgram level concentration, the additions of TCA or other acids do not result in protein precipitation, i.e., a very dilute protein solution do not precipitate in response to acids. The failure of diluted protein solutions to quantitatively precipitate have been studied over the years, unfortunately. There is still not a reliable method to quantitatively precipitate dilute protein solutions.

Most of the methods of measurement of protein concentration in solution are influenced by the presence of non-protein agents present in protein solution. Many attempts have been made to develop protein assays that will tolerate non-protein agents present in protein solution. Such methods involve removal of interfering agents from protein solution by precipitating protein out of solution. The lack of a reliable method to quantitatively precipitate a dilute protein solution has hampered the development of a protein assay that could tolerate non-protein agents present in protein solution.

Bensadoun and Weinstein (Anal Biochem. 1976, 70, 241–250.) and Peterson G. L. (Anal. Biochem. 1977, 83, 346–356) have described methods of protein assays based on precipitation of protein in dilute solutions. According to the methods, protein solution is first mixed with a solution of sodium deoxycholate and the mixture of protein and deoxycholate is precipitated by the addition of trichloroacetic acid (TCA). This method of protein precipitation does not work in protein solution containing detergents such as, Triton-X100, sodium dodecyl sulfate, (SDS) and so forth. Polacheck and Cabib ( Anal Biochem. 1981, 117, 311–314) have used RAN as a carrier to, facilitate precipitation of protein in the presence of detergents. The disadvantage of Polacheck and Cabib method is that precipitation requires a prolonged incubation period in cold followed by prolonged centrifugation at >25,000×g. Furthermore, this method of protein precipitation is not suitable for dilute protein solution containing a high concentration of detergents. Various authors have tried various techniques to improve onced Bensadoun and Weinstein method. Retz and Steele. (Anal Biochem. 1977, 79, 457–461) have tried addition of sodium dodecyl sulfate in amount nearly equivalent to that of the detergents present in protein solutions. Yen-Chung Chang (Anal. Biochem. 1992, 205, 22–26) has attempted to improve on the method of Polacheck and Cabib by addition of SDS to achieve detergent/SDS ratios at 0.67. The disadvantage of this method is that in an unknown solution, it is not easy to reach detergent/SDS ratios at 0.67 without additional investigations. Therefore, there is a need to develop a method of protein precipitation that will precipitate protein quantitatively and thus can be used for protein assays to overcome interference by non-protein agents present in protein solution.

Therefore, there is a need for developing an agent and a method of protein precipitation and a method of protein assay that could overcome interference from non-protein agents present in protein solutions.

SUMMARY OF THE INVENTION

The present invention relates to composition of a protein precipitation agent and the use of the protein precipitation agent in a method of protein precipitation. The present invention further relates to a method of protein assay using a protein precipitation agent, a method of protein assays that overcomes interference by common non-protein agents present in protein solution, and a kit for a protein assay.

An embodiment of the present invention relates to composition of a protein precipitating agent and a method of precipitation of protein in aqueous solution.

A protein precipitation agent comprising: an acidic component (agent) and a precipitate-forming component (agent), wherein said precipitate-forming component is an agent that readily forms precipitate in the presence of said acidic component.

Preferably, the protein precipitating agent may also contain a soluble salt. Preferably the salt is added into the acidic component. Preferably the salt present in the protein precipitating agents is a sodium, potassium or other common salt. Preferably, the concentration of salt provided into the protein precipitation agent is higher than 0.1M and most preferably the salt concentration is between 1–5M.

A method of protein precipitation comprising: introducing an acidic component into a protein solution followed by introduction into the mixture of protein and the acidic component a precipitate-forming component, wherein said precipitate-forming component is an agent that radially forms precipitate when come in contact with the mixture of protein and the acid component.

After a protein precipitate is formed, protein precipitate may be collected either by centrifugation or by filtration means and used for protein assay or other uses.

Preferably, the mixture of protein and the acidic component is provided with a soluble salt to encourage protein precipitation. Preferably the salt introduced into the mixture of protein and the acidic component is sodium, potassium or other common salts. Preferably, the concentration of salt is higher than 0.1M, and more preferably between 1–5M.

Yet another embodiment of the present invention relates to a method of a protein assay.

A method of a total protein assay, comprising the following steps:

(a) mixing a protein solution with an acidic component;
(b) introducing into the mixture of the protein and the acid component of the step (a) a precipitate-forming component;
(c) collecting the protein precipitate formed as a result of the introduction of the precipitate-forming component in the step (b); and
(d) combining the collected protein precipitate of the step (c) with one or more reagents of a protein assay to produce a characteristic protein color reaction.

Protein concentration is determined by measuring the density of the protein color reaction and comparing the color density with the color density of protein color reaction of a known protein concentration or protein standard.

Preferably, the mixture of the step (a) is provided with a salt. Preferably the salt provided to the mixture of protein and the acidic component is selected from a group comprising, sodium, potassium, calcium, or other common salts. Preferably, the concentration of salt provided to the mixture of protein and the acid component is higher than 0.1M. Most preferably, the concentration of salt provided to the mixture of protein and the acidic component is between 1–5M.

A further embodiment of the present invention relates to a kit for protein assay comprising: a protein precipitating agent, said protein precipitating agent comprising an acidic component and a a precipitate-forming component; and one or more reagents of a protein assay to produce characteristic protein reaction.

DESCRIPTION OF DRAWINGS

FIG. 5 shows precipitation of a wide variety of protein over a wide range of protein, concentration. Furthermore, protein assays do not show protein-to-protein variation.

PREFERRED EMBODIMENT OF THE INVENTION

Figure 1:
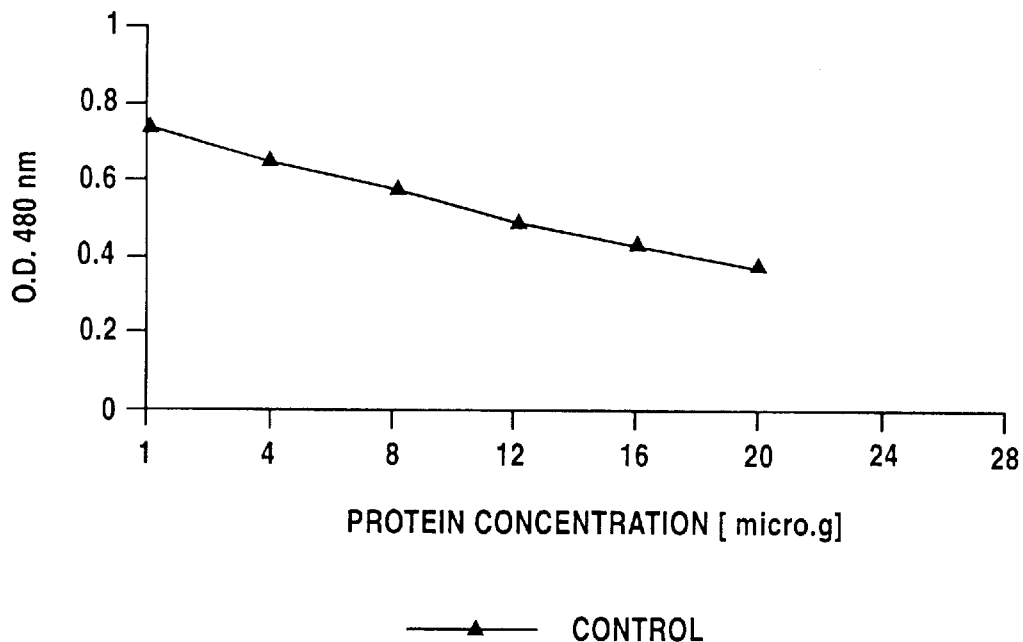
FIG. 1 shows precipitation of protein over a wide range of protein concentration using a protein precipitation agent.

The novelty of the instant invention may be appreciated from the following facts. Protein readily binds to anionic detergent deoxycholate. Deoxycholate readily precipitates in the presence of acids such as trichloroacetic acid (TCA). Thus, protein bond to deoxycholate is readily precipitated with an acid. Here, the binding of protein to deoxycholate is essential for protein precipitation. However, when a dilute protein solution contains another anionic detergent such as SDS, the addition of TCA does not precipitate protein. If deoxycholate is added to a protein solution containing SDS, and then a TCA solution is added, there is still no protein precipitate formation. If on the other hand, a dilute protein solution containing SDS is first treated with a dilute solution of TCA and then a dilute solution of deoxycholate is added, the deoxycholate and protein quantitatively co-precipitate. It has been further discovered, that dilute protein solution when treated with a wide range of organic and inorganic acidic agents can be readily precipitate with a wide range of agents that readily precipitate in the presence of an acidic agent.

According to the present invention there is provided an agent for protein precipitation. A protein precipitating agent comprising: an acidic component (agent) and a precipitate-forming component (agent), wherein said precipitate-forming component readily forms precipitate when come in contact with said acidic component.

The acidic component may be selected from organic or inorganic acids such as trichloroacetic acid (TCA), sulfosalicylic acid, hydrochloric acid, sulfuric acid, perchloric acid, and other acidic agents that substantially lower the pH toward acidic. It should be appreciated that the specification lists a few well known acidic agents, however, other types of acidic agents may be used.

The precipitate-forming component are those agents that readily form precipitate when come in contact with the acidic component of the protein precipitating agent of the instant invention. The precipitate-forming components may be selected from agents such as sodium benzoate, sodium cholate, sodium deoxycholate, or other agents that readily form precipitate in the presence of the acidic component (agents). Other salt forms of deoxycholate, cholate, and salts, particularly monovalent salts of organic acids which precipitates in acidic medium may be used as precipitate-forming agents, for example sodium salt of uric acid. The claimed invention describes a few precipitate-forming agents, however, there are other agents that readily form precipitate in the presence of acidic component and thus may be used as precipitate-forming agent.

The protein precipitating agent may also contain one or more soluble salts, salts such as sodium, potassium, calcium, magnesium, sodium sulfate, or other common salts. Most preferably, the salt used in protein precipitating agents is sodium chloride. The salt may be added either into the acidic component or into the precipitate-forming component or into both components of the protein precipitating agent (i.e., both acidic and precipitate-forming components). Most preferably, the salt is added into the acidic component (agent) of the protein precipitating agent. The concentration of salt added into the protein precipitating agents is preferably higher than 0.1M. Most preferably the concentration of salt added into the protein precipitating agents is between 1–5M.

According to the present invention there is also provided a method of protein precipitation comprising: mixing a protein solution with an acidic component; and then introducing a precipitate-forming component into the mixture of protein and the acidic component. When an acidic component is introduced into a protein solution, the mixture of the protein and the acidic component is preferably incubated for a length of time, preferably for 1–10 minutes. Upon introduction of said precipitate-forming component into the mixture of the protein and the acidic component, the protein in solution rapidly co-precipitate with the precipitates-forming component. Precipitate may be collected or harvested either by filtration or by centrifugation.

Without being bound to any particular chemical principle of protein precipitation, Applicants believe that when a dilute protein solution is treated with an acidic component, such as TCA, sulfosalicylic acid and similar agents, the protein in solution is converted to colloidal particles and such colloidal particles are not easy to precipitate. Addition of a precipitate-forming component into the mixture of a protein and an acidic agent aggregates the colloidal protein particles into larger particles which consequently co-precipitate with the precipitate-forming component.

Yet another embodiment of the present invention relates to a method of protein assay comprising the following steps:
  introducing an acidic component into a protein solution;
  introducing a precipitate-forming component into the mixture of the protein and the acidic component;
  collecting the precipitate formed as a result of the addition of the precipitate-forming component in the mixture of protein and the acidic component; and
  mixing the collected precipitate with one or more reagents of a protein assay to produce a characteristic protein reaction, preferably a color reaction.

Protein concentration is determined by reading the optical density of the protein color reaction and comparing the color density of the protein color reaction with the color density of a protein reaction of known protein concentration. Protein concentration may also be determined by measuring spectral changes in protein solution or measuring the optical density of protein solution, without any visible color, such as measuring the optical density of protein solution in ultra violet range, such as at 280 nm.

Preferably, the mixture of protein and the acidic component is provided with a salt. The salt may be provided into the mixture of protein and the acidic component by adding a salt either into the acidic component or separately into the mixture of protein and the acidic component. Most preferably, the acidic component is provided with a salt. The salt may be selected from a group comprising; sodium, potassium, magnesium or other common salts. Preferably, the salt used in the protein precipitating agents is a sodium salt, preferably, sodium chloride. The concentration of salt provided into the mixture of protein and the acidic component is preferably higher than 0.01M. Preferably, the concentration of sat provided into the mixture of protein and the acidic component is between 1–5M.

For a protein assay, after collecting protein precipitate (following the addition of a precipitate-forming component), the precipitate is preferably dissolved in an aqueous solution. Preferably, the protein precipitate is dissolved in an alkaline solution. The alkaline solution preferably containing a copper salt, preferably a copper sulfate. For a protein assay, a second protein assay reagent may be introduced into the mixture of protein-alkaline copper. The second protein assay reagent may be selected form a group consisting of; Folin reagent or bicinchoninic acid derivatives, and bathocuproine, to produce a characteristic protein color reaction.

In some cases where protein contains a detergent that forms precipitate in the presence of the acidic component, the protein solution may be treated with a concentration of an anionic detergent such as SDS (by adding a solution of SDS) prior to the addition of the acidic component into the protein solution.

Yet another embodiment of the present invention is a kit for protein assay comprising:

a protein precipitating agent; and
one or more reagents of a protein assay.

Said protein precipitating agent comprising an acidic component and a precipitate-forming component. Said protein precipitating agent may be provided with a salt. Such salt is preferably added into the acidic component, in a concentration higher that 0.1M, and most preferably in a concentration between 1–5M. The salt added to the protein precipitating agent may be selected from a group, comprising; sodium, potassium, other common salts. Preferably, the salt provided into the protein precipitating agent is a sodium salt, most preferably sodium chloride.

EXAMPLES

The invention is further explained with the help of the following examples.

Materials and Methods

Protein Solution: A protein assay was performed as follows. Unless indicated otherwise, 2 mg/ml BSA protein solution in distilled water was used in this study. Unless specified otherwise, aliquots of 1–30 $\mu$l were transferred in to (2 ml) microfuge tubes. An appropriate volumes of non-protein agents (such as detergents, reducing agents, chelating agents etc) were added to the protein samples and mixed, which created a mixture of protein solution in the presence of non-protein and/or interfering agents. In control, protein solution was not mixed with any non-protein agent, instead 100 $\mu$l pure water was added to each tube. When indicated, the protein solution used in this study was other than BSA.

Protein Assay agents: The methods of present inventions were tested using popular protein assay reagents. The tests were performed using a modification of the Lowry protein assay method (Lowry et al., J. biol. Chem., 1951, 193, 265–275) as modified and described in the U.S. Pat. No. 5,300,440, a bicinchoninic acid method of a protein assay as described by Smith et al (Anal. Biochem. 1985, 150, 76–85), and an alkaline copper-bathocuproine based protein assay as described by (Matsushita et. al. Clinica Chimica. 1993, 216, 103–111).

The reagents of the Lowry method of protein assay included: An alkaline copper solution containing a copper salt (0.05%) and sodium-potassium tartrate (0.16%) in a sodium hydroxide solution (1N), hereinafter refereed to "alkaline copper solution" and a solution of Folin-Ciocalteu reagent (5–15%).

The bicinchoninic acid method consisted of a solution A, 1% bicinchoninic acid sodium salt, 2% sodium carbonate, 0.16% sodium tartrate, 0.4% sodium hydroxide, and 0.95% sodium bicarbonate, pH 11–12. A solution B: consisted of 4% copper sulfate. Before use the solution A and B were mixed in 100 part solution A and 2 part solution B (i.e. 100:2), hereinafter referred to as "alkaline copper solution".

Copper-bathocuproine protein assay method consisted of a Solution A containing copper sulfate (0.05%) and tartrate (0.16%) in NaOH (1N), hereinafter, refereed to "alkaline copper solution". A solution-B, a color producing solution containing ascorbic acid (1.4 mM, 250 mg/L) and bathocuproine (0.65 mM, 370 mg/L bathocproinedisulfonic acid sodium salt).

Protein Precipitation Agents: Protein precipitation agents included an acidic components and a precipitate-forming component.

Acidic component: selected form a group consisting of a 1–10% solutions of trichloroacetic acid, sulfosalicylic acid, and hydrochloric acid (0.01–2N). Where indicated, a salt was added to the acidic component. The salt included such salts as sodium chloride, potassium chloride, sodium acetate magnesium chloride, etc. The salt concentrations in the range of 0–5M were tested.

Precipitate-forming component: selected form a group consisting of a 0.01–3% solutions of sodium deoxycholate, sodium cholate and sodium benzoate were used as precipitate forming agents.

Protein Precipitation: For protein precipitation, an appropriate volume of an acid component was introduced into the protein solution. Protein solution was throughly mixed with the acid component, followed by the addition of an appropriate volume of a precipitate-forming component. After the addition of precipitate-forming component, the mixture of protein, the acidic component and the precipitate-forming components were mixed. A massive precipitate was observed.

The precipitates were collected by either filtration (using spin or disk filters) or by centrifugation. When a centrifugation was used to collect the protein precipitate, the precipitate was separated from the supernatant by decanting off the supernatant.

For protein assays, the protein assay reagents were directly added to the precipitate as described in various examples. Alternatively, precipitate may be dissolved into an aqueous solution, followed by the addition of the reagent of a protein assay.

For a protein assay, the assay reagents may be directly added to the precipitate as described in various examples. Alternatively, the precipitate may be first dissolved in an aqueous solution, followed by the addition of one or more reagents of protein assays.

For a protein assay based on the Lowry method, the precipitate was preferably directly dissolved in the alkaline copper solution (of the Lowry method), followed by the addition of the Folin reagent.

For a protein assay based on the bicinchoninic acid method, the precipitate was preferably directly dissolved in the alkaline copper solution (of the bicinchoninic acid method).

For a protein assay based on the copper-bathocuproine method, the precipitate was preferably directly dissolved in the alkaline copper solution (of the copper-bathocuproine method).

Example 1

The effectiveness of a protein precipitating agent at various protein concentration was tested. Solution of TCA (10%) containing 5M NaCl was used as acidic component and sodium deoxycholate (1%) was used as precipitate-forming component.

Aliquots of 2–30 µl from a standard protein solution (2 mg/ml BSA) were transferred to microfuge tubes. 100 µl of pure water was added to each tube to dilute the protein solution by 50–30 fold. A 0.5 ml aliquot of the acidic component (10% TCA, containing 5M NaCl) was introduced into each protein solution and immediately mixed by vortexing the tubes. After mixing, a 0.5 ml aliquot of the precipitate-forming component (1% solution of sodium deoxycholate ) was introduced into each solution and mixed immediately. A large amount of precipitate was observed in each tube. Precipitates were collected by centrifuging the tube at 5000×g for 5 minutes. Supernatant was removed by inverting the tube on a clean absorbing paper. The precipitate pellets were firmly attached to the bottom of the tubes.

Protein assays: The effectiveness of protein precipitating agents was determined by a protein assay method, as follows. 100 µl of alkaline copper solution (1N NaOH containing 0.05% copper sulfate and 0.16% tartrate) was added to each precipitate, after mixing, 0.4 ml of pure water was added to each tube and mixed. 1.0 ml of color producing agent (bathocuproine) was introduced into each tube which produced a characteristic light orange color for protein reaction. The optical density of each tube was determined at 480 nm. The optical density of each tube was plotted against the amount of protein added to each tube. Results are shown in FIG. 1.

FIG. 1 shows a liner relationship between the amount of protein added to each tube and the optical density of color reaction. The result clearly indicates that the precipitating agent quantitatively precipitated protein over a wide range of protein concentration.

Example 2

The effectiveness of various acidic components was tested. Trichloroacetic acid (5–10%), sulfosalicylic acid (5%), and hydrochloric acid (0.7N) were tested as acidic component. 5M sodium chloride was added to each acidic component. A 1% solution of sodium deoxycholate was used as precipitate-forming component.

Figure 2:
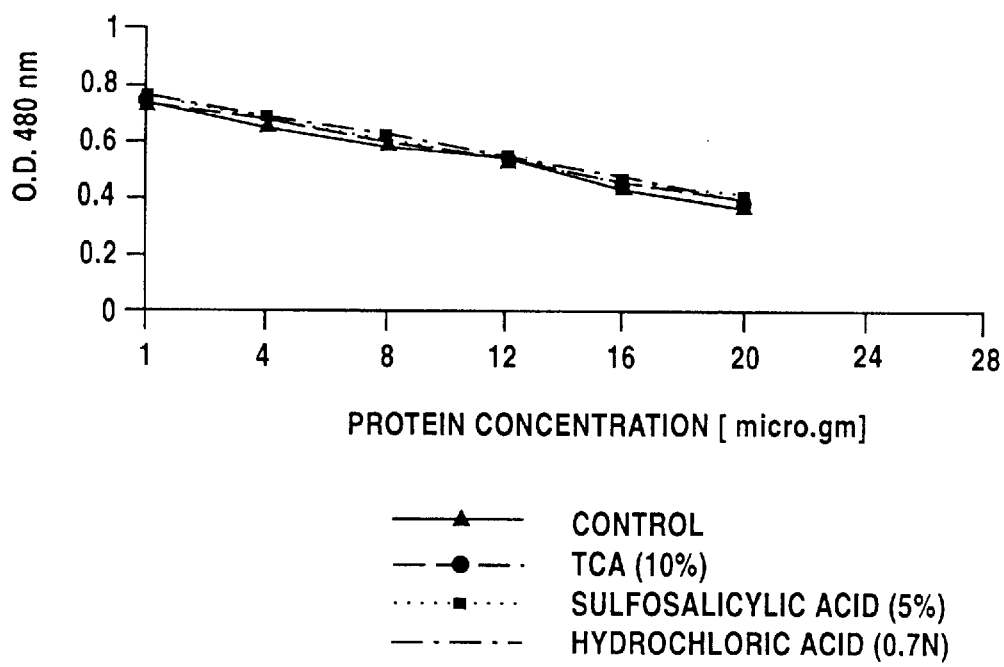
FIG. 2 shows effectiveness of various acidic components used in a protein precipitation agent.

The tests were performed as described in the Example 1, except TCA, sulfosalicylic acid and hydrochloric acid were used as acidic component. The results are shown in FIG. 2, which established that over a wide range of protein concentration the acidic component tested were effective in quantitative precipitation of protein. Tests were also performed using lower concentration of the acidic agents listed, it was found that concentration as low as 1% TCA was able to effectively precipitate protein (data not shown). However, when protein solution contained a high concentration of non-ionic detergents such as Triton-X100, TCA a concentration higher than 3% was needed for quantitative precipitation of protein.

Example 3

The effectiveness of various precipitate-forming components was tested. 10% solution of TCA containing 5M NaCl was used as acidic component. Sodium deoxycholate (1%), sodium cholate (1%) and, a sodium benzoate (2%) was tested as precipitate-forming agents.

Figure 3:
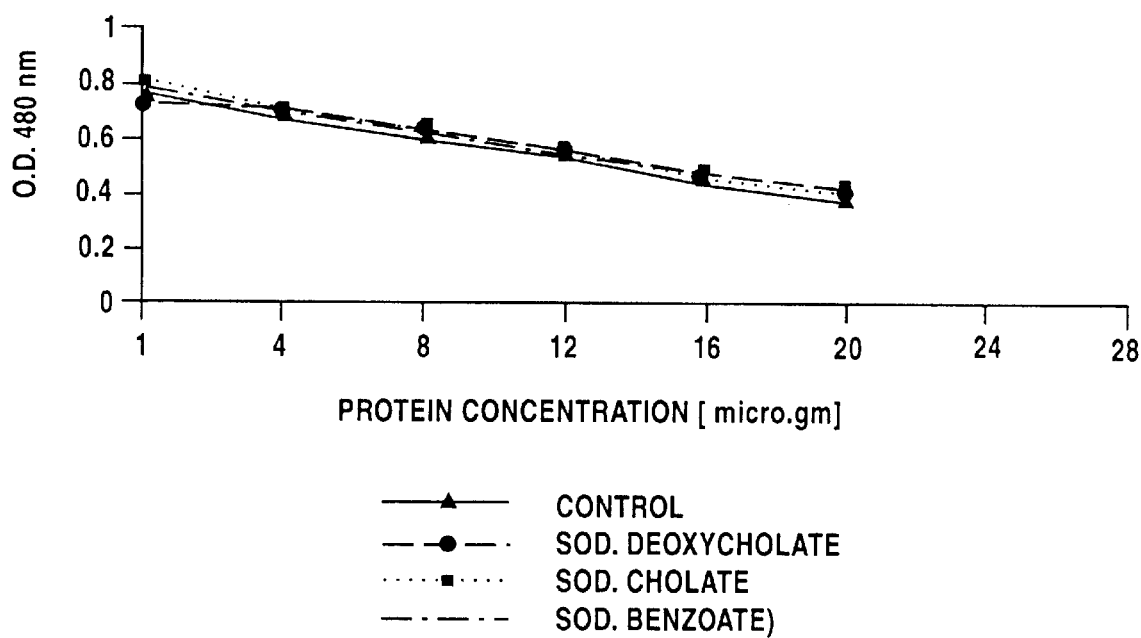
FIG. 3 shows effectiveness of various precipitate-forming components used in a protein precipitation agent.

The tests were performed as described in the Example 1, except sodium deoxycholate (1%), sodium cholate (1%) and, sodium benzoate (2%), were tested as precipitate-forming component. The results are shown in FIG. 3, which established the effectiveness of the precipitate-forming components used. Over a wide range of protein concentration, the precipitate-forming components (agents) tested were able to effectively and quantitatively precipitate the protein. Lower concentrations of the precipitate-forming were also tested. The deoxycholate as low as 0.01% was effective in precipitating protein.

Example 4

The effectiveness of protein precipitating agents in the presence of detergents such as sodium dodecyl sulfate (SDS) and Triton X100 was tested, and compared with a control protein solution without any detergent. Tests were performed as described in the Example 1. TCA (10%) containing 5M NaCl and Na-deoxycholate (1%) were used as acidic and precipitate-forming components, respectively. Test protein samples were mixed with 100 µl of SDS (1%) and 100 µl of Triton X100 (3%).

Figure 4:
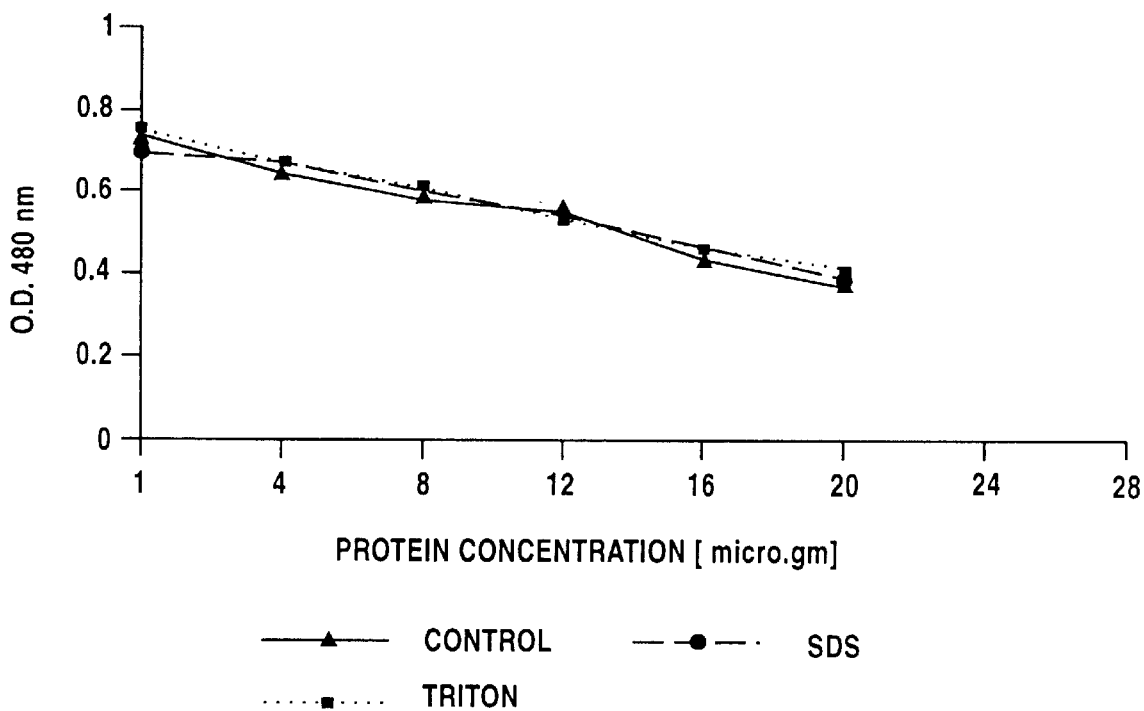
FIG. 4 shows effectiveness of protein precipitating agents in the presence of detergents

The results are shown in FIG. 4. which establishes that, over a wide range of protein concentration, the protein precipitating agent is effective even in the presence of high concentration of anionic and non-ionic detergents. A wide range of other detergents were also tested. Protein solutions containing (1–3%), Thesit, CHAPS, CHAPSO, Tween-20, Brij 30, Triton-X114, Sarcosyl, N-Octyl Glucoside, degitonin etc. have been effectively and quantitatively precipitated using the precipitating agent and as described in the instant invention.

Example 5

The effectiveness of providing a salt in an acidic component was tested. The tests were performed as described above in Example 1. TCA (10%) and deoxycholate (1%) was used as acidic and precipitate-forming components, respectively. An appropriate amount of NaCl was added to protein sample-protein samples with or without detergents (SDS and Triton X100). It was discovered that protein solution without detergent did not require addition of a salt for quantitative precipitation over a wide range of protein precipitation. However, in protein solutions containing high concentration of detergents, the addition of salt in acidic components improved quantitative precipitation of protein. Salt concentration in the range of 1–5M was found to be suitable in most cases.

Example 6

The effectiveness of various salts in protein precipitating agents was tested. Tests were performed as described in Example 5. Potassium chloride, sodium chloride, sodium sulfate, magnesium chlorides etc. have been tested. It was found that most common salts can be used to facilitate protein precipitation.

Example 7

The effectiveness of protein precipitating agents in removing non-protein agents present in protein solution was tested. The non-protein agents were selected from those agents that are known to interfere with popular protein assays. The tests were performed as described in Example 1. The following agents were tested (by introducing into test protein solution). It was discovered that the protein precipitating agent of the instant invention effectively precipitated the protein and removed the non-protein agents present in protein solution, which consequently resulted in protein assays free from interference by non-protein agents. The agents tested included urea (8M), 0.5% mercaptoethanol, DTT, guanidine hydrochloride (6), guanidine thiocyanate (6), sodium azide, glycerine, Tris-buffer, EDTA, Hepes, glycine, and a few combinations of these agents such as solution containing urea (4M), SDS and mercaptoethanol and solution containing guanidine thiocyanate, sarcosyl and mercaptoethanol.

In tests described above, successful protein assays were performed without any interference from the agents listed above.

Example 8

Test of reagents of various protein assay methods. The precipitating agent of the instant invention has been used in a various protein assay. Tests were performed as described in Example 1. After collecting protein precipitate, the precipitates were directly dissolved in the alkaline copper solutions of various protein assay methods, as described above in Material and Method section. After dissolving protein precipitate in the alkaline copper solution, an appropriate second protein assay reagent was introduced into the mixture of protein and alkaline copper solution. The second protein assay reagents were selected from a group consisting of Folin, Bicinchoninic acid and bathocuproine. The protein assay worked without any difficulty. A linear response between protein concentration and the optical density was observed (data not shown).

Example 9

The effects of a protein precipitating agent on various purified proteins. The following purified proteins have been tested. They are alchohol dehydrogenase (yeast) (AD), carbonic anhydrase (CA), thyroglobulin (TG), dog albumin (DA), sheep albumin (SA), rabbit albumin (RA), and ribonuclase (RN), and bovine gamma globulin (BGG). The tests were performed as described in Example, using 10% TCA containing 5M NaCl and 1% deoxycholate as precipitate-forming agent. Results are shown in FIG. 5. It was found that the precipitating agent of the instant invention precipitated these protein quantitatively over a wide range of protein concentration. Furthermore, the resulting protein assay showed no protein-to-protein variation.

What we claim our invention is:

1. A method of a total protein assay, comprising the following steps:

mixing a protein solution with an acidic component;

introducing into the mixture of the protein and the acidic component a precipitate-forming component to form a protein precipitate;

collecting the protein precipitate;

combining the collected protein precipitate with one or more reagents of a protein assay to produce a characteristic protein color reaction, and determining protein concentration.

2. The method of protein assay according to claim 1, wherein said acidic component is selected from a group comprising, trichloroacetic acid, sulfosalicylic acid, hydrochloric acid, and sulfuric acid.

3. The method of protein assay according to claim 1, wherein said precipitate-forming component is selected from a group comprising cholate, deoxycholate, and sodium benzoate.

4. The method of protein assay according to claim 1, wherein the protein solution is first treated with SDS prior to the addition of said acidic component.

5. The method of protein assay according to claim 1, wherein the protein precipitate is combined with an alkaline solution.

6. The method of protein assay according to claim 5, wherein the alkaline solution contains a copper salt.

7. The method of protein assay according to claim 6, wherein, after combining the precipitate with the alkaline copper solution the mixture is further combined with a second reagent of a protein assay selected from the group consisting of bathocuproine, Folin, and bicinchoninic acid.

8. The method of protein assay according to claim 1, wherein the mixture of the protein and the acidic component is provided with a salt.

9. The method of protein assay according to claim 8, wherein the salt is provided into the acidic component.

10. The method of protein assay according to claim 8, wherein the salt is provided into the precipitate-forming component.

11. The method of protein assay according to claim 8, wherein the salt provided into the mixture of the protein and the acidic component is sodium salt.

12. The method of protein assay according to claim 8, wherein the salt provided into the mixture of the protein and the acidic component is sodium chloride.

13. The method of protein assay according to claim 8, wherein the salt provided into the mixture of the protein and the acidic component has a concentration higher than 0.1M.

14. The method of protein assay according to claim 13, wherein the concentration of salt provided into the mixture of the protein and the acidic component is between 1M to 5M.

15. The method of protein assay according to claim 14, wherein the concentration of salt provided into the mixture of the protein and the acidic component is about 5M.

\* \* \* \* \*